(12) United States Patent
Wang

(10) Patent No.: US 7,415,360 B2
(45) Date of Patent: Aug. 19, 2008

(54) MULTIPARAMETER METHOD OF SCREENING FOR ATHEROSCLEROSIS-RELATED CORONARY HEART DISEASE OR STROKE

(76) Inventor: Xing Fa Wang, 16 Palm St., Worcester, MA (US) 01604-3844

( * ) Notice: Subject to any disclaimer, the term of this patent is extended or adjusted under 35 U.S.C. 154(b) by 122 days.

(21) Appl. No.: 10/810,296

(22) Filed: Mar. 27, 2004

(65) Prior Publication Data

US 2005/0216427 A1    Sep. 29, 2005

(51) Int. Cl.
G06F 19/00 (2006.01)
G06F 17/10 (2006.01)
G01N 31/00 (2006.01)
G05B 21/00 (2006.01)

(52) U.S. Cl. ............... 702/19; 700/266; 702/22; 703/2

(58) Field of Classification Search ............ None
See application file for complete search history.

(56) References Cited

OTHER PUBLICATIONS

Ravensbergen et al., The Influence Of The Angle Of Confluence On The Flow In A Vertebro-Basilar Junction Model, Journal of Biomechanics 1996, vol. 29, No. 3, pp. 281-299.*

Ballantyne et al., Role of Lipid and Lipoprotein Profiles In Risk Assessment and Therapy, The American Heart Journal, Aug. 2003, 146(2), Abstract.*

Evans et al., Medical Lipid-Regulating Therapy: Current Evidence, Ongoing Trials and Future Developments, Drugs, 2004; 64 (11), Abstract.*

* cited by examiner

*Primary Examiner*—Michael Borin
*Assistant Examiner*—Jason M Sims
(74) *Attorney, Agent, or Firm*—Harris H. Wang

(57) ABSTRACT

The present invention is a multiparameter method of screening for the diagnosis, prevention or treatment of atherosclerosis-related coronary heart disease (CHD) or stroke. This method is used for predicting a total risk of the disease and a disease risk level, determining a primary cause in the disease, assessing a therapeutic efficacy and optimizing the therapeutic targets at the different stages of the disease in different individuals who require the therapy to prevent or to treat the disease. The method of this invention can be used to combine the contributions of atherosclerotic risk factors to the disease and to unite the two major methods for diagnosing the disease: screening the Low-density lipoprotein (LDL) level and measuring the C-reactive protein (CRP) concentration in human blood. The method of this invention is written as an executable computer program named the MMA.exe © 2004, by Xing F. Wang, which provides greater ease and convenience to perform this method.

10 Claims, 2 Drawing Sheets

Figure 1

| | | |
|---|---|---|
| LDL Concentration: | 150 | mg/dL |
| CRP Concentration: | 1.5 | mg/L |
| Systolic Blood Pressure: | 170 | mmHg |
| Diastolic Blood Pressure: | 80 | mmHg |
| Heart Rate: | 90 | s^-1 |
| Artery Vessel Radius: | 1.6 | cm |
| Plasma Temperature: | 37.4 | Celsius |
| Angle: | 45 | degree |
| Diffusional Length: | 0.6 | cm |
| LDL Diffusion Coeff.: | 1.8 | cm^2/s |
| CRP Diffusion Coeff.: | 0.9 | cm^2/s |

Figure 2

| Results | | | | |
|---|---|---|---|---|
| Current Status | | Previous Status | | Evaluate |
| 0.12354652 | 0.04706943 | 0.64143107 | 0.09310353 | Back |
| 0.16553383 | 0.00319968 | 0.42536509 | 0.00639236 | |
| 0.20507113 | 0.08005968 | 0.12311088 | 0.00005966 | |
| 0.10715524 | 0.05083749 | 0.04551591 | 0.12027071 | |
| 0.06757430 | | 0.05083749 | | |
| Total Risk: 0.8200473350 | | Total Risk: 1.5860265588 | | |
| Primary Therapy Target: Systolic Pressure | | Primary Therapy Target: LDL Level | | |
| Primary Cause of Disease: High Monocyte Flux | | Primary Cause of Disease: High LDL Flux | | Theraputic Efficacy: |
| Secondary Therapy Target: CRPLevel | | Secondary Therapy Target: LDL Level | | 48.29546 % |

MULTIPARAMETER METHOD OF SCREENING FOR ATHEROSCLEROSIS-RELATED CORONARY HEART DISEASE OR STROKE

REFERENCES CITED

U.S. Patent Documents

"Not applicable"

NON-PATENT DOCUMENTS

[1] Wang et al, In Progress in atherosclerosis research: Analytical methods for atherosclerosis research. Editor Schoenhagen, Nova Science Publishers Inc., 2006, PP.33-66.
[2] Wang, Analytical models of atherosclerosis. Review. Atherosclerosis, 2001, Vol. 159, PP.1-7.
[3] Grundy, In Plasma lipoproteins and coronary artery disease: Role of low-density lipoproteins in development of coronary artery atherosclerosis. Editor Kreisberg et al., Blackwell Scientific, 1992, PP.93-124.
[4] National Cholesterol Education Program. Second report of the expert panel on detection, evaluation, and treatment of high blood cholesterol in adults (Adult treatment panel II). Circulation, 2002, Vol.106, PP.1333-1445.
[5] Shephered et al, Strategies for reducing coronary heart disease and desirable limits for blood lipid concentrations: guidelines from the British Hyperlipidaemia Association. British Medicine Journal, 1987, Vol.295, PP.1245-1246.
[6] Study group of the European Atherosclerosis Society. The recognition and management of hyperlipidaemia in adults. A policy statement of European Atherosclerosis Society. Europe Heart Journal, 1988, Vol.9, pp.571-600.
[7] Canadian lipoprotein conference at hoc committee on guidelines for dyslipoproteinemias. Guidelines for the detection of high risk lipoprotein profiles and the treatment of dyslipoproteinemias. Canada Medicine Association Journal, 1990, Vol.142, pp.1371-1382.
[8] National Center for Health Statyistics, National health and nutritional examination, 1994, Survey (III).
[9] Libby, Inflammation in atherosclerosis. Review. Nature, 2002, Vol.420, pp.868-874.
[10] Li et al, The macrophage foam cell as a target for therapeutic intervention. Review. Nature Medicine, 2002, Vol.8, pp.1235-1242.
[11] Ross et al, Mechanisms of disease: Atherosclerosis—an inflammatory disease, New England Journal Medicine, 1999, Vol.340, pp.115-126.
[12] Caro et al, Arterial wall shear and distribution of early atheroma in man. Nature, 1969, Vol.223, pp.1159-1161.
[13] Texon, Hemodynamic basis of atherosclerosis. Hemisphere Publishing Corporation, 1980.
[14] Friedman et al, Arterial geometry affects hemodynamics: a potential risk factor for atherosclerosis. Atherosclerosis, 1983, Vol.46, pp.225-231.
[15] Beere et al, Retarding effect of lowered heart rate on coronary atherosclerosis. Science, 1984, Vol.226, pp.180-182.
[16] Kannel et al, Heart rate and cardiovascular mortality: The framingham study. American Heart Journal, 1987, Vol.113, pp.1489-1494.
[17] Schwartz et al, The pathogenesis of atherosclerosis: an overview. Clilnical Cardiology, 1991, Vol.14, pp.1-16.
[18] Kruth, Lipoprotein cholesterol and atherosclerosis. Review. Current Molecular medicine, 2001, Vol.1, pp.633-653.
[19] Lusis, Atherosclerosis. Review. Nature, 2000, Vol.407, pp.233-241.
[20] Could et al., Cholesterol reduction yields clinical benefit: Impact of statin trails. Circulation, 1998, Vol.97, pp.946-952.
[21] Debakey et al, Patterns of atherosclerosis and their surgical significance. Annual Surgery, 1985, Vol.201, pp.115-131.
[22] Bargeron et al, Distribution of the geometric parameters of human aortic bifurcations. Atherosclerosis, 1986, Vol.6, pp.109-113.
[23] Ravensbergen et al., The influence of the angle of confluence ont he flow in a vertebro-basilar junciton model, Journal of Biomechanics 1996, Vol.29, No.3, pp.281-299.
[24] Ballantyne et al., Role of lipid and lipoprotein profiles in risk assessment and therapy, The american Heart Journal, 2003, August; Vol.146, No.2, Abstract.
[25] Evans et al., medical lipid-regulating therapy: Current evidence, ongoing trials and future developments, Drugs, 2004, Vol.64, No.11, Abstract.

BACKGROUND OF THE INVENTION

Atherosclerosis is a progressive disease characterized by the thickening, hardening and loss of elasticity of inner artery walls. The pathologic process underlies most coronary heart disease (CHD) and strokes.

Since atherosclerosis is a leading cause of mortality and morbidity in the world, intense research efforts have been dedicated to the disease for the past two centuries. Many researchers have been focusing on the understanding of atherosclerosis mechanism and the development of efficient screening procedures [1, 2].

Since Anitschkow, N. stated that dietary cholesterol caused atherosclerosis in 1913, over the past five decades, lipid-lowering therapy has played a central role in the prevention and treatment of atherosclerosis-related CHD or stroke. This therapeutic method treats the elevated level of low-density lipoprotein (LDL) or cholesterol in blood as a primary cause in atherosclerosis [3]. In deciding whether a patient requires the therapy to prevent or to treat the disease, physicians usually rely heavily on measuring the LDL concentration in the patient's blood. The expert panels in the USA, Europe, UK and Canada have defined the guidelines of LDL level in serum [4-7]. It was reported that there were about 55 million American adults who had elevated level of LDL that warranted intervention [8]. The lipids hypothesis emphasizes a causal relationship between the elevated LDL level and disease. However, clinical evidences indicated that many individuals in the United States developed atherosclerosis-related CHD in the absence of abnormalities in the lipoprotein profile [9].

The recent method for diagnosing the disease is the so-called the measurement of C-reactive protein (CRP) concentration in blood plasma [9-10]. The method treats atherosclerosis as an inflammatory disease. In 1852, Rokitansky, C. V. suggested that small mural thrombi existed at the arterial wall, which led to plaques. In 1856, Virchow, R. stated that an early event in atherosclerosis was an inflammatory response to an injured arterial wall. In 1973, Ross, R. and Glomset, J. combined the two hypotheses and suggested the response-to-injury hypothesis [11]. The inflammatory hypothesis emphasizes inflammation as a primary cause in atherosclerosis [9-11]. The above-mentioned two major methods for diagnosing the disease are not mutually exclusive but they cannot be united.

In 1969, Caro, C. G., et al. found that atherosclerotic lesion occurred in areas experiencing low wall shear stress [12]. In 1980, Texon, M. developed a concept called hemodynamic basis of atherosclerosis [13]. In 1983, Friedman, M. H., et al. stated a causal relationship between arterial geometry and atherosclerosis [14]. Clinical and experimental evidences indicated that the elevated level of heart rate causes atherosclerosis [15-16]. In 1991, Schwartz, C. J., et al. suggested a unifying hypothesis that focused on lesion-prone arterial sites [17]. More recently, Wang, H. H. created analytical models of atherosclerosis [2]. Kruth, H. S. emphasized increased LDL uptake into arterial walls as a primary cause in atherosclerosis [18]. However, there is no screening method that is able to determine the effects of these risk factors on the disease.

Epidemiological studies stated that many risk factors influenced atherosclerosis, mainly including elevated LDL level, hypertension, smoking cigarette, family history, systemic inflammation such as rheumatoid arthritis, infectious agents such as *Chlamydia pneumoniae*, high-fat diet and emotion factors such as depression [3, 19]. However, the contributions of these risk factors to the disease cannot be combined using current screening methods, which result in limited reliable clinical screening capabilities. In recent review article entitled "atherosclerosis", Lusis, A. J. points out that efficient screening procedures are urgently needed but they are unlikely to be available in the near future [19].

BRIEF SUMMARY OF THE INVENTION

The objective of this invention is to resolve some of the above-mentioned problems by developing a multiparameter method of screening, which is used for predicting a total risk of the disease and a disease risk level, determining a primary cause in the disease, optimizing the therapeutic targets and assessing a therapeutic efficacy for the individuals who require the diagnosis, prevention or treatment of atherosclerosis-related CHD or stroke.

The method of the invention can be used to combine the contributions of atherosclerotic risk factors to the disease. Screening the LDL level and measuring the CRP concentration in blood, the two major methods for diagnosing the disease, are united into this invention.

This invention views that atherosclerosis is a multifactor disease with differently combined risk factors dominating at different stages of the disease in different individuals and that the mass transfer flux of LDL and monocyte in blood to the arterial endothelium at the lesion-prone sites is a primary cause in the disease. Further features and advantages of this invention can be seen in the DETAILED DESCRIPTION OF THE INVENTION.

BRIEF DESCRIPTION OF THE DRAWING

FIG. 1 is a typical input screenshot of the MMA.exe showing the inputted atherosclerotic parameters including a LDL concentration parameter in mg/dL, a CRP concentration parameter in mg/L, a blood systolic pressure parameter in mmHg, a blood diastolic pressure parameter in mmHg, a heart rate parameter in $s^{-1}$, a plasma temperature parameter in ° C., an angle parameter in degree, a radius parameter of the arterial vessels in cm, and an axial position parameter of the diffusional flux in cm, called diffusional length in cm; $D_L$=the LDL diffusion coefficient in $cm^2/s$; and $D_c$=the CRP diffusion coefficient in $cm^2/s$.

FIG. 2 is a typical output screenshot of the MMA.exe showing the output including a total risk of the disease; a primary cause in the disease; a primary therapy target; a secondary therapy target; and a therapeutic efficacy for individuals who require the diagnosis, prevention or treatment of atherosclerosis-related CHD or stroke.

DETAILED DESCRIPTION OF THE INVENTION

The present invention is a multiparameter screening method that is used for combining the contributions of atherosclerotic risk factors to the disease, predicting a total risk of the disease and a disease risk level, determining a primary cause in the disease, assessing a therapeutic efficacy and optimizing the therapeutic targets at the different stages of the disease in different individuals who require the diagnosis, prevention or treatment of atherosclerosis-related CHD or stroke, which comprises the following phases:

defining the normal as free from atherosclerosis-related coronary heart disease or stroke;

the measured values refer to the quantities of atherosclerotic parameters to be measured;

an individual having the measured values of atherosclerotic parameters;

the individual having normal values of these atherosclerotic parameters;

determining the disease risks yielded by the differences betweent he measured values and the normal values of these atherosclerotic parameters;

adding all the disease risks together so as to yield a total risk of the disease;

determining a disease risk level containing the total risk of the disease;

selecting an atherosclerotic risk factor related to an atherosclerotic parameter that is the greatest contribution to the total risk so as to result in this risk factor as a primary therapy target of the disease;

determining a greater flux between the LDL mass transfer flux and the monocyte mass transfer flux so as to result in this greater flux as a primary cause in the disease;

selecting a greater concentration level between the LDL level in serum and the CRP level in blood plasma so as to result in this greater level as a secondary therapy target of the disease;

calculating a relative ratio between the current total risk from the currently measured values of these atherosclerotic parameters and the previous total risk from previously measured values of these parameters so as to yield this ratio as a therapeutic efficacy of the disease; and repeating the above-mentioned methods until the disease risk level is reduced to a normal level for the individual who requires the therapy to prevent or to treat atherosclerosis-related CHD or stroke.

the above-mentioned methods are written as an executable computer program named the MMA.exe to perform said methods.

The method of this invention comprising the steps of:

Step one: Determining the mass transfer flux of the LDL particles and monocyte cells in blood to the endothelium at the arterial bifurcations, branching, curvatures or tapering, called the lesion-prone sites, so as to result in this flux as a primary cause in the disease, which comprise:

Major clinical studies [9-10, 19] state that early atherosclerosis lesions consist of both LDL and monocytes, which are transferred from blood to the arterial endothelium and accumulated in the subendothlium.

According to these clinical evidences, the inventor has created the multifactor models of atherosclerosis using a bioheterogeneous reaction model, a natural convection model and a boundary value model [1].

These models view that the mass transfer flux of the LDL and monocytes in blood to the arterial endothelium at the lesion-prone sites is a primary cause in the disease [1].

These models are used to yield the following expression of the mass transfer flux (detailed derivation of this expression presented in inventor's notebook and reference [1])

$$J = 0.69 c_0 \left( \frac{v^3 D^{16}}{v^4} \right)^{\frac{1}{27}} \left( \frac{(g \cos\alpha + fu)k}{z} \right)^{\frac{2}{9}} \quad (A)$$

where J=the mass transfer flux of LDL or monocyte, g=the gravitational acceleration, $c_0$=the LDL or monocyte concentration in blood, f=the heart rate, v=the eddy of the blood fluid in the region at the lesion-prone sites, u=the average velocity of the blood fluid in axial direction of arterial vessels, $\nu$=the kinetic viscosity of the blood plasma, z=the axial position of diffusional flux along the inner artery wall at the sites or z is called diffusional length, $\alpha$=the angle between the average velocity and gravity, D=the diffusion coefficient, and $$k = \frac{c_0}{\rho_0} \frac{\partial \rho}{\partial c}$$

in which $\rho$=the plasma density and $\rho_0$=the blood density.

These models and expression (A) is used to help the understanding of atherosclerosis mechanism and to explain clinical and experimental results [1], which are supported by the clinical and experimental evidences [2-3, 9-10, 12-21]. This invention involves the expression (A).

Step two: Defining the atherosclerotic parameters that are related to the atherosclerotic risk factors, which comprise the steps of:

Since the CRP level in blood plasma is a marker of systemic inflammation or infectious agents [9], the leukocyte-monocyte level in blood has the form:

$$c_0 = H_e c \quad (B)$$

where c=the CRP concentration or c=the LDL concentration at $H_e$=1 and $H_e$=the parameter that is independent of c. Substituting k and (B) into (A) yields:

$$J = A c^{\frac{11}{9}} (v^3 D^{16})^{\frac{1}{27}} \left( \frac{g \cos\alpha + fu}{z} \right)^{\frac{2}{9}} \quad \text{where} \quad (1.1)$$

$$A = 0.69 H_e^{\frac{11}{9}} v^{-\frac{4}{27}} \left( \frac{1}{\rho_0} \frac{\partial \rho}{\partial c} \right)^{\frac{2}{9}}.$$

The Poiseuille law states that the average velocity of a laminar fluid is proportional to the pressure gradient and to the second power of radius of a circular tube, which is expressed by $$u = H_a p a^2 \quad (C)$$

where u=the average velocity of blood fluid, p=the blood pressure gradient, a=the radius of arterial vessels and $H_a$=the parameter that is independent of p and a.

Since the previous eddy is proportional to the average velocity of the fluid in a circular tube, the eddy has the form $$v = H_b u \quad (D)$$

where v=the eddy and $H_b$ is a parameter that is independent of u. Substituting (C) into (D) yields:

$$v = H_a H_b p a^2. \quad (E)$$

The Stokes-Einstein equation states that the diffusion coefficient is proportional to the fluid temperature, which has the form $$D = H_d T \quad (F)$$

where D=the diffusion coefficient, T=the plasma temperature and $H_d$ a parameter that is independent of T.

Substituting (C), (E) and (F) into (1.1) yields $$J = B c^{\frac{11}{9}} p^{\frac{1}{3}} T^{\frac{16}{27}} a^{\frac{2}{3}} f^{\frac{2}{9}} z^{-\frac{2}{9}} \text{ and} \quad (1.2)$$

$$J = E c^{\frac{11}{9}} D^{\frac{16}{27}} z^{-\frac{2}{9}} (\cos\alpha)^{\frac{2}{9}} \quad (1.3)$$

where J=the mass transfer flux in $10^{-5}$ g/cm$^2$s; the atherosclerotic parameters including c=the LDL concentration parameter in mg/dL or c the CRP concentration parameter in mg/L, p=the blood systolic pressure parameter in mmHg or p=the blood diastolic pressure parameter in mmHg, f=the heart rate parameter in s$^{-1}$, T=the plasma temperature parameter in °C., $\alpha$=the angle parameter in degree, a=the radius parameter of arterial vessels in cm, and z=the axial position parameter of diffusional flux in cm or z is called the diffusional length; D=the diffusion coefficient in cm$^2$/s; the conversion factor $$B = A H_a^{\frac{1}{3}} H_b^{\frac{1}{9}} H_d^{\frac{16}{27}}$$

that is independent of c, p, T, f, a and z in (1.2); and the conversion factor $$E = A g v^{\frac{3}{27}}$$

that is independent of c, D, $\alpha$ and z in (1.3).

The total mass transfer flux given by (1.1) consists of both the flux given by (1.2) under the transient inertial force=$\rho fu$ and the flux given by (1.3) under gravity=$\rho g$.

The inventor defines c, p, T, f, a, $\alpha$ and z in (1.1) or (1.2) and (1.3) as the atherosclerotic parameters because the contributions of atherosclerotic risk factors to the disease are integrated into these expressions through these atherosclerotic parameters.

Main risk factors of atherosclerosis relate closely to these atherosclerotic parameters. For example, the elevated LDL level equals an increase in the LDL concentration parameter, hypertension risk factor equals an elevated level of the systolic or diastolic pressure parameter, smoking cigarette and depression relate to an elevated level of heart rate parameter, and the CRP concentration parameter is a marker of the risk factor of systemic inflammation or infectious agents.

These atherosclerotic parameters and the expressions (1.1) or (1.2) and (1.3) are employed when performing the method of this invention.

Step three: Determining the disease risks yielded by the difference between the measured values and the normal values of these atherosclerotic parameters, which comprise the steps of:

Step 3.1:

Substituting a measured value $Cm_1$ of the LDL concentration parameter into (1.1) yields $$Jm_1 = HCm_1^{\frac{11}{9}} \text{ where}$$

$$H = A(v^3 D^{16})^{\frac{1}{27}} \left( \frac{g \cos\alpha + fu}{z} \right)^{\frac{2}{9}} \text{ and}$$

$$H_e = 1 \text{ in } A;$$

substituting a normal value $Cn_1$ of the LDL concentration into (1.1) yields $$Jn_1 = HCn_1^{\frac{11}{9}};$$

and calculating $$\frac{Jm_1 - Jn_1}{Jn_1}$$

yields:

$$R_1 = \left( \frac{Cm_1}{Cn_1} \right)^{\frac{11}{9}} - 1 \tag{1}$$

where $R_1$ is the disease risk caused by the LDL concentration parameter related to the atherosclerotic risk factors being an elevated LDL level in human serum, hypercholesterolemia, high-fat diet, or other risk factors that increase in the LDL level.

Step 3.2:

Substituting a measured value $Cm_2$ of the CRP concentration parameter into (1.1) yields $$Jm_2 = HCm_2^{\frac{11}{9}} \text{ where } H = A(v^3 D^{16})^{\frac{1}{27}} \left( \frac{g \cos\alpha + fu}{z} \right)^{\frac{2}{9}};$$

substituting a normal value $Cn_2$ of the CRP concentration into (1.1) yields $$Jn_2 = HCn_2^{\frac{11}{9}};$$

and calculating $$\frac{Jm_2 - Jn_2}{Jn_2}$$

yields:

$$R_2 = \left( \frac{Cm_2}{Cn_2} \right)^{\frac{11}{9}} - 1 \tag{2.1}$$

where $R_2$ is the disease risk caused by the CRP concentration parameter related to the atherosclerotic risk factors being the systemic inflammation, infectious agents, an elevated CRP level in human blood plasma, or other risk factors that increase the CRP level.

Step 3.3:

Determining an equivalent factor F between the $R_1$ in Step 3.1 and the $R_2$ in Step 3.2, which comprises the following two methods:

1. The First Method:

Substituting the LDL diffusion coefficient $D_L$ into (1.1) yields $$J_x = MD_L^{\frac{16}{27}} \text{ where } M = Ac^{\frac{11}{9}} v^{\frac{3}{27}} \left( \frac{g \cos\alpha + fu}{z} \right)^{\frac{2}{9}}$$

and $J_x$=the LDL mass transfer flux;

substituting the CRP diffusion coefficient $D_c$ into (1.1) yields $$J_y = MD_c^{\frac{16}{27}}$$

where $J_y$=the CRP mass transfer flux;

taking $$J_y D_L^{\frac{16}{27}} = J_x D_c^{\frac{16}{27}}$$

so as to yield:

$$J_y = J_x F \tag{G}$$

where the equivalent factor $$F = \left( \frac{D_c}{D_L} \right)^{\frac{16}{27}};$$

and according to (G), the equation (2.1) in Step 3.2 is rewritten as $$R_2 = F \left( \left( \frac{Cm_2}{Cn_2} \right)^{\frac{11}{9}} - 1 \right) \tag{2}$$

where the disease risk $R_2$ caused by the difference between the measured value Cm and normal value Cn of the CRP concentration parameter corresponds to the disease risk $R_1$ caused by the LDL concentration parameter by means of (2).

2. The Secondary Method:

The equivalent factor F=0.66, which will be yielded in the Step five of the DETAILED DESCRIPTION OF THE INVENTION.

Step 3.4:

Substituting a measured value $Pm_3$ of the blood systolic pressure parameter into (1.2) yields $$Jm_3 = H_p Pm_3^{\frac{1}{3}} \text{ where } H_p = Bc^{-\frac{11}{9}} T^{\frac{16}{27}} a^{\frac{2}{3}} f^{\frac{2}{9}} z^{-\frac{2}{9}};$$

substituting a normal value $Pn_3$ of the systolic pressure into (1.2) yields $$Jn_3 = H_p P_3^{\frac{1}{3}};$$

and calculating $$\frac{Jm_3 - Jn_3}{Jn_3}$$

yields:

$$R_3 = \left(\frac{Pm_3}{Pn_3}\right)^{\frac{1}{3}} - 1 \qquad (3)$$

where $R_4$ is the disease risk caused by the systolic pressure parameter related to atherosclerotic risk factors being an elevated level of the systolic pressure, family history of hypertension, or other risk factors that increase in the systolic pressure.

Step 3.5:

Substituting a measured value $Pm_4$ of the blood diastolic pressure parameter into (1.2) yields $$Jm_4 = H_p Pm_4^{\frac{1}{3}} \text{ where } H_p = Bc^{-\frac{11}{9}} T^{\frac{16}{27}} a^{\frac{2}{3}} f^{\frac{2}{9}} z^{-\frac{2}{9}};$$

substituting a normal value $Pn_4$ of the diastolic pressure into (1.2) yields $$Jn_3 = H_p P_3^{\frac{1}{3}};$$

and calculating $$\frac{Jm_3 - Jn_3}{Jn_3}$$

yields:

$$R_4 = \left(\frac{Pm_4}{Pn_4}\right)^{\frac{1}{3}} - 1 \qquad (4)$$

where $R_5$ is the disease risk caused by the diastolic pressure parameter related to the atherosclerotic risk factors being an elevated level of the diastolic pressure, the family history of hypertension, or other risk factors that increase in the diastolic pressure.

Step 3.6:

Substituting a measured value $Fm_5$ of the heart rate parameter into (1.2) yields $$Jm_4 = H_p Pm_4^{\frac{1}{3}} \text{ where } H_p = Bc^{-\frac{11}{9}} T^{\frac{16}{27}} a^{\frac{2}{3}} f^{\frac{2}{9}} z^{-\frac{2}{9}};$$

substituting a normal value $Fn_5$ of the heart rate into (1.2) yields $$Jn_5 = H_f Fn_5^{\frac{2}{9}};$$

and calculating $$\frac{Jm_3 - Jn_3}{Jn_3}$$

yields:

$$R_5 = \left(\frac{Fm_5}{Fn_5}\right)^{\frac{2}{9}} - 1 \qquad (5)$$

where $R_6$ is the disease risk caused by the heart rate parameter related to the atherosclerotic risk factors being an elevated level of the heart rate, smoking cigarette, emotional factors such as depression, or other risk factors that increase the heart rate.

Step 3.7:

Substituting a measured value $Am_6$ of the radius parameter of arterial vessel into (1.2) yields $$Jm_6 = H_a Am_6^{\frac{2}{3}} \text{ where } H_a = Bc^{-\frac{11}{9}} T^{\frac{16}{27}} f^{\frac{2}{9}} p^{\frac{1}{3}} z^{-\frac{2}{9}};$$

substituting a normal value $An_6$ of the arterial radius into (1.2) yields $$Jn_6 = H_a An_6^{\frac{2}{3}};$$

and calculating $$\frac{Jm_6 - Jn_6}{Jn_6}$$

yields:

$$R_6 = \left(\frac{Am_6}{An_6}\right)^{\frac{2}{3}} - 1 \quad (6)$$

where $R_7$ is the disease risk caused by the arterial radius parameter related to atherosclerotic risk factors being the increased radius of arterial vessels at the lesion-prone sites, or other risk factors that increase the arterial radius.

Step 3.8:

Substituting a measured value $Tm_7$ of the plasma temperature parameter into (1.2) yields $$Jm_7 = H_T Tm_7^{\frac{16}{27}} \text{ where } H_T = Bc^{\frac{11}{9}} a^{\frac{2}{3}} f^{\frac{2}{9}} p^{\frac{1}{3}} z^{-\frac{2}{9}};$$

substituting a normal value $Tn_7$ of the plasma temperature into (1.2) yields $$Jn_7 = H_T Tn_7^{\frac{16}{27}};$$

and calculating $$\frac{Jm_6 - Jn_6}{Jn_6}$$

yields:

$$R_7 = \left(\frac{Tm_7}{Tn_7}\right)^{\frac{16}{27}} - 1 \quad (7)$$

where $R_8$ is the disease risk caused by the plasma temperature parameter related to the atherosclerotic risk factors being the elevated temperature of the blood plasma in the region of the lesion-prone sites, the elevated body temperature-related diseases, or other risk factors that increase the plasma temperature.

Step 3.9:

Substituting a measured value $\alpha_m$ of the angle parameter into (1.3) yields $$Jm_8 = H_\alpha (\cos\alpha m_8)^{\frac{2}{9}} \text{ where } H_\alpha = Ec^{\frac{11}{9}} D^{\frac{16}{27}} z^{-\frac{2}{9}};$$

substituting a normal value $\alpha_n$ of the angle into (1.3) yields $$Jn_8 = H_\alpha (\cos\alpha n_8)^{\frac{2}{9}};$$

and calculating $$\frac{Jm_8 - Jn_8}{Jn_8}$$

yields:

$$R_8 = \left(\frac{\cos\alpha m_8}{\cos\alpha n_8}\right)^{\frac{2}{9}} - 1 \quad (8)$$

where $R_9$ is the disease risk caused by the angle parameter related to the atherosclerotic risk factors being the reduced size of the angle between the gravity and the average velocity of blood fluid in the region of the lesion-prone sites, an acute daughter angle of arterial bifurcation, or other risk factors that reduce the angle size.

Step 3.10:

Substituting a measure value $Z_m$ of the axial position parameter of the diffusional flux into (1.1) yields $$Jm_9 = H_z Zm_9^{-\frac{2}{9}} \text{ where } H_z = Ac^{\frac{11}{9}} (v^3 D^{16})^{\frac{1}{27}} (g\cos\alpha + fu)^{\frac{2}{9}};$$

substituting a normal value $Z_n$ of the diffusional length into (1.1) yields $$Jn_9 = H_z Z_n^{-\frac{2}{9}};$$

and calculating $$\frac{Jm_9 - Jn_9}{Jn_9}$$

yields $$R_9 = \left(\frac{Zn_9}{Zm_9}\right)^{\frac{2}{9}} - 1 \quad (9)$$

where $R_{10}$ is the disease risk caused by the axial position parameter of diffusional flux related to the atherosclerotic risk factors being the reduced axial position of the diffusional flux along the inner arterial wall at the lesion-prone sites, or other risk factors that reduce the axial position.

Step Four:

Adding the $R_1$ in step 3.1 and the $R_2$ in step 3.3 through the $R_{10}$ in step 3.10 together so as to yield a total risk of the disease comprising;

a current total risk of the disease caused by the differences between the currently measured values and the normal values of the atherosclerotic parameters;

a previous total risk of the disease caused by the differences between the previously measured values and the normal values of the atherosclerotic parameters.

Step Five:

Determining a disease risk level containing the total risk of the disease in Step four comprising;

considering the range of the LDL concentration in serum from 100 mg/dL to 300 mg/dL; and dividing the LDL risk level into the six risk sublevels at intervals of 33 mg/dL according to the guideline of LDL risk level given by the expert panels on US National Cholesterol Education Program;

considering the range of CRP concentration in blood plasma from 1.0 mg/L to 4.0 mg/L; and dividing the CRP risk level into the six risk sublevels at intervals of 0.5 mg/L according to the guideline of the CRP risk level given by American Heart Association;

calculating the ratio between the LDL range and the CRP range yields an equivalent factor $F=2/3=0.66$;

Substituting the F=0.66, $C_n$ mg/L and the six CRP measured vales that equal the interval values of six CRP risk sublevels into the equation (2) in Step 3.3 respectively; and calculating (2) yields the six disease risks as the interval values of the six disease risk sublevels respectively;

doubling these interval values so as to result in the following seven disease risk sublevels caused by combining the LDL flux and the monocyte flux: $0.84 \geq$ first disease risk level $\geq 0.00$, $1.75 \geq$ second disease risk level $>0.84$, $2.70 \geq$ third disease risk level $>1.75$, $3.70 \geq$ fourth disease risk level $>2.70$, $4.70 \geq$ fifth disease risk level $>3.70$, $5.80 \geq$ sixth disease risk level $>4.70$ and seventh disease risk level $>5.80$; and selecting a disease risk level containing the total risk of the disease in Step four from among seven of the disease risk sublevels.

Step six: Selecting an atherosclerotic risk factor related to the atherosclerotic parameter that is the greatest contribution to the total risk of the disease in Step four so as to result in this risk factor as a primary therapy target of the disease.

Step seven: selecting a greater flux between the LDL mass transfer flux and the monocyte mass transfer flux so as to result in this greater flux as a primary cause in the disease, said method comprising the steps of:

selecting the LDL mass transfer flux as a primary cause in the disease when $R_1$ in Step $3.1 \geq R_2$ in Step 3.3; or selecting the monocyte mass transfer flux as a primary cause in the disease when $R_1$ in Step $3.1 < R_2$ in Step 3.3;

Step eight: Selecting an greater level between a measured value of the LDL concentration parameter in Step 3.1 and a measured value of the CRP concentration parameter in Step 3.2 so as to result in this greater level as a secondary therapy target of the disease, said method comprising the steps of:

selecting the LDL concentration level in serum as a secondary therapy target of the disease when $R_1$ in Step $3.1 \geq R_2$ in Step 3.3; or selecting the CRP concentration level in blood plasma as a secondary therapy target of the disease when $R_1$ in Step $3.1 < R_2$ in Step 3.3;

Step nine: Calculating a relative ratio between the current total risk of the disease and the previous total risk of the disease in Step four so as to yield this ratio as a therapeutic efficacy of the disease.

Step ten: Repeating the method in Step three through the method in Step nine until the disease risk level is reduced to a normal level for the individual who requires the therapy to prevent or to treat atherosclerosis-related CHD or stroke.

Step eleven: These methods in Step three through Step nine are written as an executable computer program named said MMA.exe to be installed into a general purpose digital computer device to accomplish these methods.

EXAMPLES

Example 1

An individual having a measured value of the LDL level in serum of 150 mg/dL and a measured value of the CRP concentration in blood plasma of 2.3 mg/L.

Inputting these measured values into said MMA.exe so as to yield the following first output for the individual: a total risk of the disease is 1.82 or 182% in which the disease risk caused by the LDL concentration parameter is 0.64 or 64% and the disease risk caused by the CRP concentration parameter is 1.18 or 118%; a third disease risk level; a primary cause in disease being the monocyte mass transfer flux; a primary therapy target being systemic inflammation such as rheumatoid arthritis, infectious agents or other risk factors that increase the CRP level.

After treating systemic inflammation, the patient's CRP level is reduced to 1.6 mg/L from 2.3 mg/L and the following second output yielded by said MMA.exe: a total risk of the disease is 1.16 or 116% in which the disease risk caused by the CRP level is reduced to 0.52 from 1.18; a second disease risk level; a primary cause in disease being the LDL mass transfer flux; a therapeutic efficiency of 36.32%; a primary therapy target being the elevated LDL level in blood, high-fat diet or other risk factors that increase the LDL level.

This example shows that the method of this invention can be widely used for clinical practices in atherosclerosis-related CHD or stroke because screening the LDL level and measuring the CRP level in blood, the two major methods for diagnosing the disease, have been united into this invention.

Example 2

An individual having a measured value of the LDL concentration in serum of 110 mg/dL, a measured value of blood systolic pressure of 195 mmHg, a measured heart rate of 85 $s^{-1}$ and a measured value of the CRP level in blood plasma of 1.2 mg/L.

Inputting these measured values into said MMA.exe so as to yield the following first output for the individual: a total risk of the disease of 0.503 or 50.3%; a first disease risk level; a primary cause in disease being the monocyte mass transfer flux; a primary therapy target being the elevated level of the systolic pressure, the family history of hypertension or other risk factors that increase the systolic pressure; a secondary therapy target being the systemic inflammation or other risk factors that increase the CRP level.

After treating the hypertension, the individual's systolic pressure is reduced to 160 mmHg from 195 mmHg and the following second output yielded by said MMA.exe: a total risk of the disease is reduced to 0.428 or 42.8% from 0.503 or 50.3%; a first disease risk level; a primary cause in the disease being the monocyte mass transfer flux; a therapeutic efficacy of 14.9%, a primary therapy target being the systemic inflammation or other risk factors that increase the CRP level; and a secondary therapy target being the elevated LDL level in blood or other risk factors that increase the LDL level.

This example shows that the method of this invention is reliable because it can be used to combine the contributions of multiple risk factors of atherosclerosis to the disease.

Example 3

The major clinical study [20] stated that a 1.0% reduction in an individual's total LDL level in blood led to a 1.5% reduction in the risk of atherosclerosis-related CHD. Said MMA.exe yields that a 1.0% reduction in the LDL level results in a 1.22% reduction in this risk. This example indicates that the method of this invention is strongly supported by the clinical evidence.

Example 4

Autopsy and clinical studies [13-14, 17, 21] suggested that regions of arterial bifurcations had the greatest predilection for atherosclerosis. However, the current screening method such as screening LDL or cholesterol levels in the patients' blood is unable to determine the contribution of the arterial geometry to the disease. Internal angles among 70 human aortic bifurcations can vary widely from 10° to 70° [22]. Different internal angles may lead to different angle α in (1.3).

An individual A having a measured angle $\alpha_1$ being 15°, an individual B having a measured angle $\alpha_2$ being 45° and the two persons having a 1% increase in the LDL level in blood. Using said MMA.exe, this invention predicts a 7.2% lower total risk for 45° than for 15°. This risk from difference in the bifurcation's internal angles is significantly lower than the 1.5% reduction in risk from 1% reduction in LDL level [20], which indicates that the arterial geometry in certain instances can play a greater role in atherosclerosis than simply LDL level.

In the example, the method of this invention reveals that atherosclerosis is a multifactor disease with differently combined risk factors dominating in different individuals.

Example 5

The first step is inputting the currently measured values, the previously measured values and the normal values of the individual's atherosclerosis parameters into the input screen of said MMA.exe showing in FIG. 1. The second step is pressing the "update" button and "calc. risk" button of the input screen and finally, pressing the "evaluate" button of the output screen so as to yield a typical output screen showing in FIG. 2.

This output from said MMA.exe containing a total risk of the disease; a primary cause in the disease; a primary therapy target; a secondary therapy target; and a therapeutic efficacy for individuals who require the therapy to prevent or treat atherosclerosis-related CHD or stroke.

This example indicates that said MMA.exe can perform this method of this invention with greater ease and convenient.

The Main Advantages of the Invention are:

The method of this invention allows physician to predict a total risk of the disease and a disease risk level; to determine a primary cause in the disease; to assess the therapeutic efficacy and to optimize the therapeutic targets at the different stages of disease in different individuals who require the diagnosis, the prevention or the treatment of atherosclerosis-related CHD or stroke.

The method of this invention is reliability because it can be used to combine the contributions of atherosclerotic risk factors to the disease.

The method of this invention is efficient because it views atherosclerosis-related CHD or stroke as a multifactor disease with differently combined risk factors dominating at the different stages of disease in different individuals, which is supported by major clinical and experimental evidences [3, 10, 13-21].

The method of this invention can be widely used for the clinical practices in atherosclerosis-related CHD or stroke because screening the LDL level and measuring the CRP concentration in blood, the two major methods for diagnosing the disease, have been united into this invention.

The method of the invention is written as an executable computer program named said MMA.exe that provides greater ease and convenience to perform this method.

While a specific embodiment of the invention has been show and described in detail to illustrate the application of the principles of the invention, it will be understood that the invention may be embodied otherwise without departing from such principles and that various screening methods, alternative executable computer program, and equivalents will occur to those skilled in the art given the benefit of this disclosure. Thus, the invention is not limited to the specific embodiment described herein, but is defined by the appended claims.

I claim:

1. A multiparameter screening Method for atherosclerosis-related coronary heart disease (CHD) or stroke comprising;
    defining the disease as atherosclerosis-related CHD or stroke;
    defining the normal as tree from said disease;
    defining the following parameters as atherosclerotic parameters consisting of c=the Low-density lipoprotein (LDL) concentration parameter in mg/dL or c=the C-reactive protein (CRP) concentration parameter in mg/L, p=the blood systolic pressure parameter in mmHg or p=the blood diastolic pressure parameter in mmHg, f=the heart rate parameter in $s^{-1}$, a=the radius parameter along arterial radius in cm, T=the temperature parameter of blood plasma in ° C., α=the angle parameter between the gravity and the mean velocity of blood fluid in arterial vessels in degree and z =the axial length. parameter of diffusion flux along the inner wall in the axial direction of arterial vessels in cm, called the diffusion length parameter;
    measuring, for an individual, the values of said atherosclerotic parameters presented in the following expressions:

$$J = Ac^{\frac{11}{9}}(v^3 D^{16})^{\frac{1}{27}}\left(\frac{g\cos\alpha + fu}{z}\right)^{\frac{2}{9}} \text{ or} \quad (1.1)$$

$$J = Bc^{\frac{11}{9}} p^{\frac{1}{3}} T^{\frac{16}{27}} a^{\frac{2}{3}} f^{\frac{2}{9}} z^{-\frac{2}{9}} \text{ and} \quad (1.2)$$

$$J = Ec^{\frac{11}{9}} D^{\frac{16}{27}} z^{-\frac{2}{9}}(\cos\alpha)^{\frac{2}{9}} \quad (1.3)$$

wherein J=the mass transfer flux in $10^{-5}$ g/(cm$^2$s), A, B and E=the constants of conversion factors, v=the eddy velocity of blood fluid in arterial vessels in cm/s, u=the mean velocity of the blood fluid in cm/s, D =the diffusion coefficient in cm$^2$/s, and g=the gravitational acceleration in cm/s$^2$;
    measuring, for an individual not having the disease, the normal values of said atherosclerotic parameters;

determining the disease risks yielded by the difference between said measured values and said normal values of said atherosclerotic parameters;

adding all said disease risks containing a total risk of said disease;

determining a disease risk level containing said total risk of said disease;

selecting an atherosclerotic risk factor related to an atherosclerotic parameter having the greatest contribution, to said total risk of said disease so as to result in said risk factor as a primary therapy target of said disease;

selecting a greater flux between the LDL mass transfer flux and the monocyte mass transfer flux so as to result in said greater flux as a primary cause in said disease;

selecting a greater concentration level between the LDL level in the serum and the CR2 level in the blood plasma so as to result in said greater level as a secondary therapy target of said disease;

calculating a relative ratio between currently said total risk and previously said total risk so as to yield said relative ratio as a therapeutic efficacy of said disease;

repeating abovementioned methods until said disease risk level to reduce to a normal level for the individual who requires a therapy to prevent or to treat atherosclerosis-related CHD or stroke;

above-mentioned methods are written as an executable computer program named the MMA.exe, or another name, to be installed into a general purpose digital computer device to accomplish said methods; and outputting said total risk, said risk level, said primary cause, said therapeutic target and said therapeutic efficiency to a user or a display.

2. A method as in claim 1, wherein the nine disease risks are yielded by the differences between the measured values and the normal values of the nine atherosclerotic parameters, wherein:

substituting a measured value, $Cm_1$ in mg/dL, of the individual's LDL concentration in human serum, wherein said $Cm_1$ is determined using a medical technique for measuring the concentration of blood constituents or said $Cm_1$ is determined by the physician, into eq. 1.1 yields $$Jm_1 = HCm_1^{\frac{11}{9}} \text{ where } H = A(v^3 D^{16})^{\frac{1}{27}} \left( \frac{g\cos\alpha + fu}{z} \right)^{\frac{2}{9}},$$

substituting a normal value, $Cn_1$ in mg/dL, of said LDL concentration parameter, wherein said $Cn_1$ is determined by the physician or said $Cn_1=100$ mg/dL for adult, into eq. 1.1 yields $$Jn_1 = HCn_1^{\frac{11}{9}},$$

calculating $$\frac{Jm_1 - Jn_1}{Jn_1}$$

yields:

$$R_1 = \left( \frac{Cm_1}{Cn_1} \right)^{\frac{11}{9}} - 1 \tag{1}$$

where $Cm_1 \geq Cn_1$, and calculating (1) yields the disease risk $R_1$ caused by the LDL concentration parameter related to the atherosclerotic risk factors being an elevated LDL concentration in human serum, highfat diet, hypercholesterolemia or other risk factors that increase said LDL concentration;

substituting a measured value, $Cm_2$ in mg/L, of the individual's CRP concentration in human blood plasma, wherein said $Cm_2$ is determined using a medical technique for measuring the concentration of blood constituents or said $Cm_2$ is determined by the physician, into eq. 1.1 yields $$Jm_2 = HCm_2^{\frac{11}{9}} \text{ where } H = A(v^3 D^{16})^{\frac{1}{27}} \left( \frac{g\cos\alpha + fu}{z} \right)^{\frac{2}{9}},$$

substituting a normal value, $Cn_2$ in mg/L, of said CRP concentration parameter, wherein said $Cn_2$ is determined by the physician or said $Cn_2=1.0$ mg/L for adult, into eq. 1.1 yields $$Jn_2 = HCn_2^{\frac{11}{9}},$$

calculating $$\frac{Jm_2 - Jn_2}{Jn_2}$$

yields:

$$R_2 = F\left[ \left( \frac{Cm_2}{Cn_2} \right)^{\frac{11}{9}} - 1 \right] \tag{2}$$

where $Cm_2 \geq Cn_2$, the equivalent factor $$F = \left( \frac{D_c}{D_L} \right)^{\frac{16}{27}},$$

$D_c$=the CRP diffusion coefficient, $D_L$=the LDL diffusion coefficient, and calculating (2) yields the disease risk 1% caused by the CRP concentration parameter related to the atherosclerotic risk factors being an elevated CRP level in human blood plasma, systemic inflammation, infectious agents or other risk factors that increase said CRP level;

substituting a measured value, $Pm_3$ in mmHg, of the individual's blood systolic pressure, wherein said $Pm_3$ is determined using a medical technique for measuring the human blood pressure or said $Pm_3$ is determined by the physician, into eq. 1.2 yields $$Jm_3 = H_p Pm_3^{\frac{1}{3}} \text{ where } H_p = Bc^{\frac{11}{9}} T^{\frac{16}{27}} a^{\frac{2}{3}} f^{\frac{2}{9}} z^{-\frac{2}{9}},$$

substituting a normal value, $Pn_3$ in mmHg, of said systolic pressure parameter, wherein said $Pn_3$ is determined by the physician or said $Pn_3=120$ mmHg for adult, into eq. 1.2 yields $$Jn_3 = H_p Pn_3^{\frac{1}{3}},$$

calculating $$\frac{Jm_3 - Jn_3}{Jn_3}$$

yields:

$$R_3 = \left(\frac{Pm_3}{Pn_3}\right)^{\frac{1}{3}} - 1 \quad (3)$$

where $Pm_3 \geq Pn_3$, and calculating (3) yields the disease risk $R_3$ caused by the systolic pressure parameter related to the atherosclerotic risk factors being an elevated level of blood systolic pressure, family history of hypertension or other risk factors that increase said systolic pressure;

substituting a measured value, $Pm_4$ in mmHg, of the individual's blood diastolic pressure, wherein said $Pm_4$ is determined using a medical technique for measuring the human blood pressure or said $Pm_4$ is determined by the physician, into eq. 1.2 yields $$Jm_4 = H_p Pm_4^{\frac{1}{3}} \text{ where } H_p = Bc^{\frac{11}{9}} T^{\frac{16}{27}} a^{\frac{2}{3}} f^{\frac{2}{9}} z^{-\frac{2}{9}},$$

substituting a normal value, $Pn_4$ in mmHg, of said blood diastolic pressure parameter, wherein said $Pn_4$ is determined by the physician or said $Pn_4=70$ mmHg for adult, into eq. 1.2 yields $$Jn_4 = H_p Pn_4^{\frac{1}{3}},$$

calculating $$\frac{Jm_4 - Jn_4}{Jn_4}$$

yields:

$$R_4 = \left(\frac{Pm_4}{Pn_4}\right)^{\frac{1}{3}} - 1 \quad (4)$$

where $Pm_4 \geq Pn_4$, and calculating (4) yields the disease risk $R_4$ caused by the diastolic pressure parameter related to the atherosclerotic risk factors being an elevate level of blood diastolic pressure, family history of hypertension or other risk factors that increase said diastolic pressure;

substituting a measured value, $Fm_5$ in s$^{-1}$, of the individual's heart rate, wherein said $Fm_5$ is determined using a medical technique for measuring the human heart rate or said $Fm_5$ is determined by the physician, into eq. 1.2 yields $$Jm_5 = H_f Fm_5^{\frac{2}{9}} \text{ where } H_f = Bc^{\frac{11}{9}} T^{\frac{16}{27}} a^{\frac{2}{3}} p^{\frac{1}{3}} z^{-\frac{2}{9}},$$

substituting a normal value, $Fn_5$ in s$^{-1}$, of said heart rate parameter, wherein said $Fn_5$ is determined by the physician or said $Fn_5=72$ per minute for adult, into eq. 1.2 yields $$Jn_5 = H_f Fn_5^{\frac{2}{9}},$$

calculating $$\frac{Jm_5 - Jn_5}{Jn_5}$$

yields:

$$R_5 = \left(\frac{Fm_5}{Fn_5}\right)^{\frac{2}{9}} - 1 \quad (5)$$

where $Fm_5 \geq Fn_5$, and calculating (5) yields the disease risk $R_5$ caused by the heart rate parameter related to the atherosclerotic risk factors being an elevated level of heart rate, smoking cigarette, depression or other risk factors that increase said heart rate;

substituting a measured radius value, $Am_6$ in cm, of the individual's arterial vessel at the lesion-prone sites of arterial bifurcations, arterial branching, arterial curvatures or arterial tapering, wherein said $Am_6$ is determined using a medical technique for measuring the sizes of arterial vessels or said $Am_6$ is determined by the physician, into eq. 1.2 yields $$Jm_6 = H_a Am_6^{\frac{2}{3}} \text{ where } H_n = Bc^{\frac{11}{9}} T^{\frac{16}{27}} f^{\frac{2}{9}} p^{\frac{1}{3}} z^{-\frac{2}{9}},$$

substituting a normal value, $An_6$ in cm, of said arterial radius parameter, wherein said $An_6$ is determined by the physician or said $An_6$=a value between 0.2 cm and 2.2 cm for adult, into eq. 1.2 yields $$Jn_6 = H_a An_6^{\frac{2}{3}},$$

calculating $$\frac{Jm_6 - Jn_6}{Jn_6}$$

yields:

$$R_6 = \left(\frac{Am_6}{An_6}\right)^{\frac{2}{3}} - 1 \quad (6)$$

where $Am_6 \geq An_6$, and
- calculating (6) yields the disease risk $R_6$ caused by the arterial radius parameter related to the atherosclerotic risk factors being an increased size of arterial radius at said lesion-prone sites or other risk factors that increase the size of said arterial radius;
- substituting a measured temperature value, $Tm_7$ in ° C., of the individual's plasma fluid in the region at said lesion-prone sites, wherein said $Tm_7$ is determined using a medical technique for measuring the temperature of human blood plasma or said $Tm_7$ is determined by the physician, into eq. 1.2 yields $$Jm_7 = H_T Tm_7^{\frac{16}{27}} \text{ where } H_T = Bc^{\frac{11}{9}} a^{\frac{2}{3}} f^{\frac{2}{9}} p^{\frac{1}{3}} z^{-\frac{2}{9}},$$

substituting a normal value, $Tn_7$ in ° C., of said plasma temperature parameter, wherein said $Tn_7$ is determined by the physician or said $Tn_7=37$° C., into eq. 1.2 yields $$Jn_7 = H_T Tn_7^{\frac{16}{27}},$$

calculating $$\frac{Jm_7 - Jn_7}{Jn_7}$$

yields:

$$R_7 = \left(\frac{Tm_7}{Tn_7}\right)^{\frac{16}{27}} - 1 \quad (7)$$

where $Tm_7 \geq Tn_7$, and
- calculating (7) yields the disease risk $R_7$ caused by the plasma temperature parameter related to the atherosclerotic risk factors being an elevated temperature of said human blood plasma at said lesion-prone sites, elevated body temperature related diseases or other risk factors that increase said plasma temperature;
- substituting a measured value, $\alpha m_8$ in degree, of the angle between the gravity and the average velocity of the blood fluid in the region at said lesion-prone sites, wherein said $\alpha m_8$ is determined using a medical technique for measuring the human arterial geometries or said $\alpha m_8$ is determined by the physician, into eq. 1.3 yields $$Jm_8 = H_a(\cos\alpha\, m_8)^{\frac{2}{9}} \text{ where } H_a = Ec^{\frac{11}{9}} D^{\frac{16}{27}} z^{-\frac{2}{9}},$$

substituting a normal value, $\alpha n_8$ in degree, of said angle parameter, wherein said $\alpha n_9$ is determined by the physician or said $\alpha n_8$=a value between the 10° and 60° for adult, into eq. 1.3 yield $$Jn_8 = H_a(\cos\alpha\, n_8)^{\frac{2}{9}},$$

calculating $$\frac{Jm_8 - Jn_8}{Jn_8}$$

yields:

$$R_8 = \left(\frac{\cos\alpha m_8}{\cos\alpha n_8}\right)^{\frac{2}{9}} - 1 \quad (8)$$

where $\alpha n_8 \geq \alpha m_8$, and
- calculating (8) yields the disease risk $R_8$ caused by the angle parameter related to the atherosclerotic risk factors being a reduced size of said angle or other risk factors that reduce said angle size; and
- substituting a measured value, $Zm_9$ in cm, of the individual's axial length of diffusion flux along the inner arterial wall at said lesion-prone sites, wherein said $Zm_9$ is determined using a medical technique for measuring the human arterial geometries or said $Zm_9$ is determined by the physician, into eq. 1.1 yields $$Jm_9 = H_z Zm_9^{-\frac{2}{9}} \text{ where } H_z = Ac^{\frac{11}{9}}(v^3 D^{16})^{\frac{1}{27}}(g\cos\alpha + fu)^{\frac{2}{9}},$$

substituting a normal value, $Zn_9$ in cm, of said axial length parameter, wherein said $Zn_9$ is determined by the physician or said $Zn_9$=a value between 0.10 cm and 1.00 cm, into eq. 1.1 yields $$Jn_9 = H_z Zn_9^{-\frac{2}{9}},$$

calculating $$\frac{Jm_2 - Jn_9}{Jn_9}$$

yields:

$$R_9 = \left(\frac{Zn_9}{Zm_9}\right)^{\frac{2}{9}} - 1 \quad (9)$$

where $Zn_9 \geqq Zm_9$, and calculating (9) yields the disease risk $R_9$ caused by the axial diffusion length parameter related to the atherosclerotic risk factors being a decrease in said axial length of the diffusion flux or other risk factors that decrease said diffusion length.

3. The method of claim 2, further comprising: adding said all nine disease risks $R_1$ to $R_9$ containing a total risk of said disease consisting;

a current total risk of said disease related to the currently measured values of said atherosclerotic parameters; and a previous total risk of said disease related to the previously measured values of said atherosclerotic parameters.

4. The method of claim 3, further comprising: determining a disease risk level containing said total risk of said disease comprising:

dividing the disease risk level into the following seven risk sublevels: $0.84 \geqq$ first disease risk level $\geqq 0.00$, $1.75 \geqq$ second disease risk level $> 0.84$, $2.70 \geqq$ third disease risk level $> 1.75$, $3.70 \geqq$ fourth disease risk level $> 2.70$, $4.70 \geqq$ fifth disease risk level $> 3.70$, $5.80 \geqq$ sixth disease risk level $> 4.70$ and seventh disease risk level $> 5.80$; and selecting a disease risk level containing said total risk of said disease from among seven of said disease risk sublevels.

5. The method of claim 3, further comprising: selecting an atherosclerotic risk factor related to the atherosclerotic parameter having the greatest contribution to said total risk of said disease so as to result in said risk factor as a primary therapy target of said disease.

6. The method of claim 2, further comprising: selecting a greater flux between the LDL mass transfer flux and the monocyte mass transfer flux so as to result in said greater flux as a primary cause in said disease comprising:

selecting the LDL mass transfer flux as a primary cause in said disease when said $R_1$ said $R_2$; or selecting the monocyte mass transfer flux as a primary cause in said disease when said $R_1 <$ said $R_2$.

7. The method of claim 2, further comprising: selecting a greater concentration level between the LDL level in the human serum and the CRP level in the human blood plasma so as to result in said greater level as a secondary therapy target comprising:

selecting the LDL level in the serum as a secondary therapy target of said disease when said $R_1 \geqq$ said $R_2$; or selecting the CRP level in the plasma as a secondary therapy target of said disease when said $R_1 <$ said $R_2$.

8. The method of claim 3, further comprising: calculating a relative ratio between said current total risk of said disease and said previous total risk of said disease so as to yield said relative ratio as a therapeutic efficacy of said disease.

9. The method of claim 1, further comprising: said method containing the steps of: the step 1 of calculating $$R_1 = \left(\frac{Cm_1}{Cn_1}\right)^{\frac{11}{9}} - 1$$

yields the disease risk $R_1$ wherein $Cm_1$ is a measured value of the individual's LDL concentration in human serum, $Cn_1$ is a normal value of the LDL concentration parameter and $Cm_1 \geqq Cn_1$; calculating $$R_2 = F\left(\left(\frac{Cm_2}{Cn_2}\right)^{\frac{11}{9}} - 1\right)$$

yields the disease risk $R_2$ wherein $Cm_2$ is a measured value of the individual's CRP concentration in human blood plasma, $Cn_2$ is a normal value of the CRP concentration parameter, $$F = \left(\frac{D_c}{D_L}\right)^{\frac{16}{27}},$$

$D_C$=the CRP diffusion coefficient, DL=the LDL diffusion coefficient and $Cm_2 \geqq Cn_2$; calculating $$R_3 = \left(\frac{Pm_3}{Pn_3}\right)^{\frac{1}{3}} - 1$$

yields the disease risk $R_3$ wherein $Pm_3$ is a measured value of the individual's blood systolic pressure, $Pn_3$ is a normal value of the blood systolic pressure parameter and $Pm_3 \geqq Pn_3$; calculating $$R_4 = \left(\frac{Pm_4}{Pn_4}\right)^{\frac{1}{3}} - 1$$

yields the disease risk $R_4$ wherein $Pm_4$ is a measured value of the dividual's blood diastolic pressure, $Pn_4$ is a normal value at the blood diastolic pressure parameter and $Pm_4 \geqq Pn_4$; calculating $$R_5 = \left(\frac{Fm_5}{Fn_5}\right)^{\frac{2}{9}} - 1$$

yields disease risk $R_5$ wherein $Fm_5$ is a measured value of the individual's heart rate, $Fn_5$ is a normal value of the heart rate parameter and $Fm_5 \geqq Fn_5$; calculating $$R_6 = \left(\frac{Am_6}{An_6}\right)^{\frac{2}{3}} - 1$$

yields disease risk $R_6$ wherein $Am_6$ is a measured radius value of the individual's arterial vessel at the lesion-prone sites of arterial bifurcations, arterial branching, arterial curvatures or arterial tapering, $An_6$ is a normal value at said arterial radius parameter and $Am_6 \geqq An_6$; calculating $$R_7 = \left(\frac{Tm_7}{Tn_7}\right)^{\frac{16}{27}} - 1$$

yields the disease risk $R_7$ wherein $Tm_7$ is a measured temperature value of the individual's plasma fluid in the region at said lesion-prone sites, $Tn_7$, is a normal value of said plasma temperature parameter and $Tm_7 \geqq Tn_7$; calculating $$R_8 = \left(\frac{\cos \alpha m_8}{\cos \alpha n_8}\right)^{\frac{2}{9}} - 1$$

yields disease risk $R_8$ wherein $\alpha m_8$ is a measured value of the angle between the gravity and the average velocity of the blood fluid in the region at said lesion prone sites, $\alpha n_8$ is a normal value of the angle parameter and $\alpha n_8 \geq \alpha m_8$; and calculating $$R_9 = \left(\frac{Zn_9}{Zm_9}\right)^{\frac{2}{9}} - 1$$

yields disease risk $R_9$ wherein $Zm_9$ is a measured value of the individual's axial length of diffusion flux along the inner arterial wall at said lesion-prone sites, $Zn_9$ is a normal value of said axial diffusion length parameter and $Jn_9 \geq Jm_9$;

the step 2 of adding all nine disease risks $R_1$ to $R_9$ in the step 1 containing a total risk of said disease consisting of a current total risk of said disease related to the currently measured values of the atherosclerotic parameters and a previous total risk of said disease related to the previously measured values of the atherosclerotic parameters;

the step 3 of selecting a disease risk level containing said total risk of said disease in the step 2 from following among seven of the disease risk sublevels: $0.84 \geq$ first disease risk level $\geq 0.00$, $1.75 \geq$ second disease risk level $> 0.84$, $2.70 \geq$ third disease risk level $> 1.75$, $3.70 \geq$ fourth disease risk level $> 2.70$, $4.70 \geq$ fifth disease risk level $> 3.70$, $5.30 \geq$ sixth disease risk level $> 4.70$ and seventh disease risk level $> 5.80$;

the step 4 of selecting an atherosclerotic risk factor related to an atherosclerotic parameter having the greatest contribution to said total risk of said disease in the step 2 so as to result in said risk factor as a primary therapy target of said disease;

the step 5 of selecting the LDL mass transfer flux as a primary cause in said disease when said $R_1$ in the step $1 \geq$ said $K_2$ in the step 1 or selecting the monocyte mass transfer flux as a primary cause in said disease when said $R_1 <$ said $R_2$;

the step 6 of selecting the LDL level in human serum as a secondary therapy target of said disease when said $R_1$ in the step 1 said $R_2$ in the step 1 or selecting the CRP level in human blood plasma as a secondary therapy target of said disease when said $R_3 <$ said $R_2$; and the step 7 of calculating a relative ratio between said current total risk of said disease in the step 2 and said previous total risk of said disease in the step 2 so as to yield said relative ratio as a therapeutic efficacy of said disease; and wherein the step 1 through the step 7 are written as an executable computer program named the MMA.exe, or another name, to be installed into a general purpose digital computer device to accomplish said method and to output a result of said method to a display or to a user comprising:

starting the MMA.exe program on said device;

inputting the currently measured values, the previously measured values and the normal values of the individual's atherosclerosis parameters into the input screen of said MMA.exe by using the keyboard of said device;

clicking the "update" button and the "calc. risk" button of said input screen;

clicking the "evaluate" button of the MMA.exe output screen; and outputting said output screen to a display or to a user by using said computer device so as to produce a result of said method, called the screening report containing a total risk of said disease, a disease risk level, a primary cause in said disease, a primary therapy target of said disease, a secondary therapy target of said disease and a therapeutic efficiency, to the individual who requires a therapy to prevent or to treat atherosclerosis-related CED or stroke.

10. The method of claim 9, further comprising: repeating said method accomplished by using said device until the individual's disease risk level to reduce to a normal level for the individual who requires a therapy to prevent or to treat atherosclerosis related CHD or stroke.

* * * * *